US011918711B2

(12) United States Patent
Kim

(10) Patent No.: US 11,918,711 B2
(45) Date of Patent: Mar. 5, 2024

(54) AEROGEL CARRYING ACTIVE MATERIAL AND COMPOSITE OF HYDROGEL AND THE AEROGEL

(71) Applicant: Industry-University Cooperation Foundation Hanyang University, Seoul (KR)

(72) Inventor: Tae Won Kim, Seoul (KR)

(73) Assignee: Industry-University Cooperation Foundation Hanyang University, Seoul (KR)

( * ) Notice: Subject to any disclaimer, the term of this patent is extended or adjusted under 35 U.S.C. 154(b) by 901 days.

(21) Appl. No.: 16/962,878

(22) PCT Filed: Jan. 21, 2019

(86) PCT No.: PCT/KR2019/000826
§ 371 (c)(1),
(2) Date: Jul. 17, 2020

(87) PCT Pub. No.: WO2019/143205
PCT Pub. Date: Jul. 25, 2019

(65) Prior Publication Data
US 2020/0345882 A1 Nov. 5, 2020

(30) Foreign Application Priority Data

Jan. 19, 2018 (KR) .................. 10-2018-0006942
Jan. 21, 2019 (KR) .................. 10-2019-0007487

(51) Int. Cl.
| | | |
|---|---|---|
| *C08J 3/075* | (2006.01) | |
| *A61L 9/04* | (2006.01) | |
| *C08J 3/20* | (2006.01) | |
| *C08J 3/24* | (2006.01) | |
| *C08K 7/16* | (2006.01) | |
| *C08K 9/12* | (2006.01) | |
| *C08K 11/00* | (2006.01) | |

(52) U.S. Cl.
CPC ............... *A61L 9/048* (2013.01); *C08J 3/075* (2013.01); *C08J 3/203* (2013.01); *C08J 3/242* (2013.01); *C08K 7/16* (2013.01); *C08K 9/12* (2013.01); *C08K 11/00* (2013.01)

(58) Field of Classification Search
CPC ....... C01B 33/159; C01B 33/158; C08K 7/24; C08K 7/16; C08K 9/12; C08K 13/00; C08J 3/075; C08J 3/203; C08J 3/24; C08J 3/242; C08J 2305/04; A61L 9/048; C08L 5/04
USPC .......................................... 512/2, 1
See application file for complete search history.

(56) References Cited

U.S. PATENT DOCUMENTS

2014/0065229 A1\* 3/2014 Giray .................. B01J 13/0091
424/490

FOREIGN PATENT DOCUMENTS

| CN | 101534870 | \* | 4/2015 |
|---|---|---|---|
| KR | 10-2001-0092463 A | | 10/2001 |
| KR | 10-2010-0089632 A | | 8/2010 |
| KR | 10-2017-0128949 A | | 11/2017 |

OTHER PUBLICATIONS

St. John et al, CN 101534870 Machine Translation, Apr. 8, 2015 (Year: 2015).\*
Seda Giray et al., "Controlled drug delivery through a novel PEG hydrogel encapsulated silica aerogel system", Journal of Biomedical Materials Research A, May 2012, pp. 1307-1315, vol. 100A, Issue 5.
International Search Report of PCT/KR2019/000826 dated May 30, 2019 [PCT/ISA/210].

\* cited by examiner

*Primary Examiner* — Jessica Whiteley
(74) *Attorney, Agent, or Firm* — Sughrue Mion, PLLC

(57) ABSTRACT

An aerogel carrying an active material, and a composite of a hydrogel and the aerogel are provided. The method for preparing the composite according to the present invention comprises the steps of preparing a plurality of aerogel particles having an active material in the pores, preparing a polymer solution in which a polymer is dissolved in a water-soluble solvent, preparing an aerogel/polymer dispersion by homogenizing after mixing the aerogel particles in the polymer solution, and preparing an aerogel/hydrogel composite carrier by mixing the dispersion with a crosslinking agent solution. According to the present invention, by producing a hydrogel composite in which a plurality of aerogel particles is distributed, a complex carrier in which oil and moisture can be carried simultaneously without any surfactant can be provided. Furthermore, a composite carrier having improved properties such as low density, high strength, high component content and stable desorption can be prepared.

11 Claims, 9 Drawing Sheets

AEROGEL CARRYING ACTIVE MATERIAL AND COMPOSITE OF HYDROGEL AND THE AEROGEL

CROSS REFERENCE TO RELATED APPLICATIONS

This application is a National Stage of International Application No. PCT/KR2019/000826, filed Jan. 21, 2019, claiming priorities to Korean Patent Application No. 10-2018-0006942, filed Jan. 19, 2018 and Korean Patent Application No. 10-2019-0007487, filed Jan. 21, 2019.

TECHNICAL FIELD

The present invention relates to an aerogel, and more particularly, to an aerogel carrying an active material, and a composite of a hydrogel and the aerogel.

BACKGROUND ART

Aerogel, which was first developed in 1931, is formed by replacing a liquid part of a gel with gas. It is an ultra-light porous material and is known to be made of metal oxides such as silica, alumina, titania, zirconia, iron oxide; carbon; or agar. The aerogel may be applied to various fields such as architecture, industry, cosmetics, and biochemistry.

These aerogels are used in various industrial fields, such as construction, insulation materials for construction, and acoustic retardants as they have heat insulation, sound insulation, and electromagnetic wave shielding properties owing to their high micro porosity (U.S. Pat. No. 6,136,216 and US 2010/0275617).

DISCLOSURE

Technical Problem

The problem to be solved by the present invention is to provide a composite carrier capable of supporting both oil and moisture without a surfactant and a method for manufacturing the same. In addition, it is to provide a composite carrier having improved properties such as low density, high strength, high component content and stable desorption.

Another problem to be solved by the present invention is to provide an aerogel composite capable of further improving the performance of an active material having functionality such as scent diffusing.

Technical Solution

One aspect of the present invention provides a method for preparing an aerogel composite. The method for preparing the aerogel composite comprises preparing a plurality of aerogel particles having an aerogel particle containing particle clusters and pores formed by a porous network of the particle clusters, and an active material supported in the pores; preparing a polymer solution in which a polymer is dissolved in a water-soluble solvent; mixing the plurality of aerogel particles into the polymer solution and then homogenizing the mixture to prepare an aerogel/polymer dispersion; and mixing the dispersion with a crosslinking agent solution to prepare an aerogel/hydrogel composite carrier.

1 to 10 parts by weight of the active material may be mixed with 1 part by weight of the aerogel particle in the step of preparing the plurality of aerogel particles. The active material may be a natural extract, a natural extract oil, an alcohol having 1 to 40 carbon atoms, an alkane or an organic compound having an ester functional group having 4 to 40 carbon atoms.

The polymer may be dissolved in the water-soluble solvent and crosslinked by the crosslinking agent in the crosslinking agent solution. 0.1 to 10 parts by weight of the aerogel particles may be mixed with 10 part by weight of the polymer solution. The aerogel/polymer dispersion may be dripped into the crosslinking agent solution to form the carrier having a spherical shape when the aerogel/hydrogel composite carrier is prepared. The aerogel/hydrogel composite carrier includes a hydrogel having a three-dimensional network structure formed by crosslinking the polymer and the plurality of aerogel particles dispersed in the network structure.

Another aspect of the present invention provides an aerogel composite. The aerogel composite comprises a hydrogel having a three-dimensional network structure, and a plurality of aerogel particles having an aerogel particle including particle clusters and pores formed in a porous network of the particle clusters, and an active material supported in the pores.

The active material may be a natural extract, a natural extract oil, an alcohol having 1 to 40 carbon atoms, an alkane or an organic compound having an ester functional group having 4 to 40 carbon atoms. The composite may be a carrier having a spherical shape.

Another aspect of the present invention provides an aerogel. The aerogel comprises an aerogel particle having particle clusters and pores formed in a porous network of the particle clusters, and an active material supported on the pores. The aerogel particle may be a hybrid aerogel particle. The hybrid aerogel particle shows all of a Si—O—Si group, a Si—$CH_3$ group, and an OH group on Fourier-transform infrared spectrum.

Advantageous Effects

According to the present invention as described above, it is possible to provide a composite carrier capable of supporting both oil and moisture without a surfactant by manufacturing a hydrogel composite in which a plurality of aerogel particles are distributed in a hydrogel. In addition, it is possible to provide a composite carrier having improved properties such as low density, high strength, high component content and stable desorption.

According to the present invention, an aerogel composite including an aerogel having both hydrophobicity and hydrophilicity and an active material supported therein is provided to improve the functionality of the active material, specifically scent diffusing properties.

The advantageous effects of embodiments of the present invention are not limited to the advantageous effects mentioned above, and other advantageous effects of the present invention can be clearly understood from the description below.

MODES OF THE INVENTION

Hereinafter, embodiments of the present invention will be described in detail with reference to the accompanying drawings.

While the present invention allows for various modifications and variations, specific embodiments thereof are illustrated by the drawings, which will be described in detail below. However, it is not intended to limit the invention to the particular forms disclosed, but rather the invention includes all modifications, equivalents, and substitutes consistent with the spirit of the invention as defined by the claims.

Preparation of Aerogel Carrying Active Material

Figure 1A:
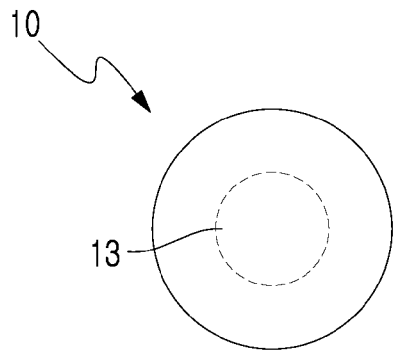
FIG. 1A is a schematic view schematically showing an aerogel according to a first embodiment of the present invention.
Figure 1B:
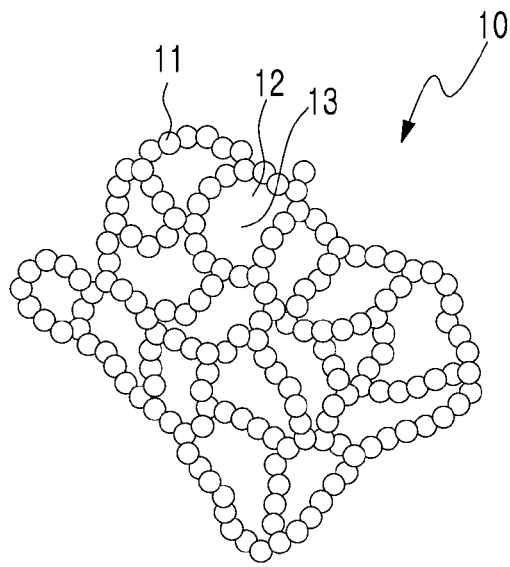
FIG. 1B is a schematic view showing the enlarged view of FIG. 1A.

FIG. 1A is a schematic view schematically showing an aerogel according to a first embodiment of the present invention, and FIG. 1B is a schematic view showing the enlarged view of FIG. 1A.

Referring to FIG. 1A, an aerogel of the present invention is provided with a plurality of aerogel particles 10, the aerogel particle 10 may have a structure in which a plurality of pores of a nanometer size are dispersed and an active material 13 is supported in the pores.

Specifically, referring to FIG. 1B, the aerogel particle 10 may include a porous network of particle clusters 11 and pores 12 in the network. The aerogel particle 10 may be formed by gathering the particle clusters 11, and the overall shape thereof may be an irregular shape. Here, the diameter of the aerogel particle 10 may be the diameter of the circumscribed sphere, and this diameter may be micrometer-sized. For example, the aerogel particle 10 may have a diameter of 0.1 to 1000 μm, specifically a few to several tens of μm, for example, 1 to 40 μm.

The surface area by the BET method of the aerogel particles 10 may be 300 to 2000 m²/g, specifically 500 to 1000 m²/g, the density thereof may be 0.03 to 0.5 g/cc, the porosity thereof may be 70 to 99%, and the pore size thereof may be 5 to 50 nm. As an example, the aerogel particles 10 may be silica aerogel particles.

The aerogel particles 10 may be hydrophobic aerogel particles having a hydrophobic surface, hydrophilic aerogel particles having a hydrophilic surface, or hybrid aerogel particles having a hydrophobic surface and a hydrophilic surface simultaneously. The hydrophobic aerogel particle may have a hydrophobic surface in the pores inside the particle in addition to the outer surface of the particle, and the hydrophilic aerogel particle may also have a hydrophilic surface in the pores inside the particle in addition to the outer surface of the particle. In addition to this, the hybrid aerogel particle may have both of a hydrophobic surface and a hydrophilic surface in the pores inside the particle as well as the outer surface of the particle.

In one example, the aerogel particles 10 may be a mixture containing both hydrophilic aerogel particles, hydrophobic aerogel particles, and hybrid aerogel particles. In this mixture, the hybrid aerogel particles may be contained at about 25 to 40 wt %, the hydrophilic aerogel particles may be contained at about 25 to 40 wt %, and the hydrophobic aerogel particles may be contained at about 25 to 40 wt %. In one embodiment, the hybrid aerogel particles, the hydrophilic aerogel particles, and the hydrophobic aerogel particles may be contained in a weight ratio of 1:1:1.

The hydrophobic aerogel particle may mainly have hydrophobic functional groups, for example, hydrogen, a C1-C18 linear or branched alkyl group, a silyloxy group, or a combination thereof. The hydrophilic aerogel particle may mainly have a hydrophilic functional group, for example, a hydroxyl group (—OH) on its surface. The hybrid aerogel particle may have both of the hydrophobic functional group and the hydrophilic functional group on its surface.

Specifically, the hybrid aerogel particles may be those in which the hydrophilic functional group and the hydrophobic functional group (R) are bonded to Si atoms, which are components of the aerogel particles. The hydrophilic functional group may be a hydroxyl group (—OH). The hydrophobic functional group (R) may be hydrogen, a C1-C18 linear or branched alkyl group, a silyloxy group represented by Chemical Formula 1 below, or a combination thereof.

  [Chemical Formula 1]

In Chemical Formula 1,
R¹ is a C1-C18 linear or branched alkyl group,
n is an integer from 0 to 3,
* may represent a bond linked to Si in the aerogel particles.

When n is an integer of 1 to 3, the functional group represented by Chemical Formula 1 may be referred to as an alkylsilyloxy group. The C1-C18 linear or branched alkyl group may be a C1-C6 linear alkyl group, or a C1-C6 linear alkyl group may be a saturated linear alkyl group, for example, methyl, ethyl, n-propyl, n-butyl, n-pentyl, or n-hexyl. For example, the C1-C6 linear alkyl group may be a methyl group or an ethyl group. In one embodiment, the hybrid aerogel particles may have hydrophobic functional groups (R) and hydrophilic functional groups (OH) on their surfaces in a molar ratio of 7:3 to 3:7.

The active material 13 may be absorbed in the aerogel particles 10, and specifically, may be supported in the pores 12 of the aerogel particles 10 to exhibit functionality, and may be a liquid material at room temperature. Here, the functionality of the active material 13 may mean, for example, fragrance supply, nutrition supply, skin protection, treatment, drugs, etc., but is not limited thereto, and the active material 13 may be a hydrophobic active material or a hydrophilic active material, but is not limited thereto if it exhibits the above functionality.

The active material may be a natural extract or a natural extract oil, for example, alfalfa extract, algae extract, almond oil, apricot kernel oil, arnica oil, borage oil, or mineral oil.

The active material may be an alcohol having 1 to 40 carbon atoms, for example, methanol, ethanol, propyl alcohol, isopropyl alcohol, glycol, butylene glycol, glycerin; an alkane having 4 to 40 carbon atoms, for example, isodecane, isohexadecane, liquid paraffin, hydrogenated polyisobutene, polyalkylene oxide, specifically, polyethylene glycol; or an organic compound having an ester functional group, for example, isopropyl myristate, alkyl benzoate, capric triglyceride, isopropyl palmitate, polymethyl methacrylate.

The active material may be a fragrance oil, for example, cottonseed oil, lavender essential oil, vanilla oil, cinnamon oil, citronella oil, goji berry fragrance oil, orange oil, mandarin orange oil, apple seed oil, Caribbean teakwood oil, cedar oil, sandalwood oil, Juniper oil, nutmeg oil, star anise oil, patchouli oil, rose oil, clove oil, saffron oil, lavender oil, rosemary oil, clary sage oil, lemon oil, peppermint oil, sweet basil oil, bergamot oil, camellia oil (or tea seed oil), blue chamomile oil, catnip oil, bay leaf oil, clementine oil, coffee essential oil, coconut oil, oregano oil, ylang-ylang oil, neroli essential oil, bergamot essential oil, rose petal oil, jasmine essential oil, vetiver essential oil, citrus essential oil, olibanum essential oil, petitgrain oil, sweet orange oil, myrrh essential oil, coriander seed oil, or frankincense oil.

For example, the active material 13 may be a hydrophobic active material, specifically, oils, more specifically, oils capable of evaporating fragrance components, that is, fragrance oils.

As an example, the aerogel of the present invention may be used as a fragrance product by itself. The aerogel may further improve the scenting characteristics, such as scenting performance and scent persistency, compared to the previously used fragrance oil.

As an example, the aerogel of the present invention is a hybrid aerogel including a hybrid aerogel particle 10 having both hydrophobicity and hydrophilicity at the same time and an active material 13 carried or supported by the hybrid aerogel particle 10. The active material 13 may be a hydrophobic active material, specifically, oils, more specifically, oils that can evaporate a fragrance component, that is, scentable. The hybrid aerogel has the characteristics of hydrophobicity and hydrophilicity at the same time, so that the evaporation rate can be adjusted, and fragrance durability can be improved compared to the case in which fragrance oil is used alone. In addition, it is possible to further improve the scenting performance and scent persistency compared to the case of using a hydrophobic aerogel. In addition, scent performance and scent persistency can be further improved by controlling the amount and fraction of the hybrid aerogel particles and fragrance oil in the hybrid aerogel composite.

The aerogel composite carrying the active material of the present invention may be manufactured by preparing the aerogel particles and mixing the aerogel particles and the active material.

The method of manufacturing the hybrid aerogel particles may be as follows. However, it is not limited thereto. First, a hydrophobic aerogel powder having hydrophobic aerogel particles may be prepared. The hydrophobic aerogel powder can be prepared by modifying the surface of a hydrogel to hydrophobic, followed by drying and grinding.

The hydrophobic aerogel powder may be heat-treated to partially modify the outer surface and further the surface of the inner pores of the particles provided in the powder. Specifically, the hydrophobic surface functional groups of at least some of the particles provided in the hydrophobic aerogel powder may be changed to hydrophilic surface functional groups. Specifically, the hydrophobic surface functional groups such as hydrogen, an alkyl group or a silyloxy group, specifically an alkylsilyloxy group, can be converted to a hydroxyl group by heat treatment. At the same time, residual moisture in the aerogel powder can be at least partially or completely removed.

The heat treatment of the hydrophobic aerogel powder may include a temperature increase step of gradually raising the temperature of the hydrophobic aerogel powder, and a sintering step of leaving the hydrophobic aerogel powder in a heated state for a predetermined time to sinter the hydrophobic aerogel powder.

Accordingly, as described above, at least some of the particles of the hydrophobic aerogel powder may be converted into hybrid aerogel particles having both hydrophobic surfaces and hydrophilic surfaces, and some other particles may be converted into hydrophilic aerogel particles having hydrophilic surfaces, and some other particles may remain as hydrophobic aerogel particles that maintain hydrophobic surfaces. As a result, it is possible to obtain an aerogel powder that is a mixture containing all of hydrophilic aerogel particles, hydrophobic aerogel particles, and hybrid aerogel particles.

When the hydrophobic aerogel includes an alkyl group ($CH_3$), the hydrophobic aerogel has a larger particle size and a smaller pore volume and a smaller pore surface area than a hydrophilic aerogel. As the alkyl group is oxidized to generate a hydroxyl group, the size of the aerogel particles is reduced as the size of the functional group is reduced, and the pore volume and the surface area of the pores can increase. Therefore, the hydrophilicity may be increased by increasing the space capable of absorbing moisture.

The heat treatment may be performed using an electric furnace, and may be performed for 0.5 to 24 hours in a state where the temperature is raised to a temperature of 300 to 500° C. In addition, the heat treatment may be performed in an oxidizing atmosphere, specifically, an air atmosphere. As an example, changing only some hydrophobic surface functional groups of the hydrophobic aerogel to hydrophilic surface functional groups may be performed through heat treatment of about 345 to 355° C., specifically 347 to 353° C. Forming hydrophilic aerogel in which all of the hydrophobic surface functional groups of the hydrophobic aerogel has been changed into hydrophilic surface functional groups may be performed through heat treatment of about 356 to 365° C., specifically 357 to 363° C.

The aerogel composite may be prepared by physical mixing the aerogel particles 10 and the active material 13, for example, mixing in a bowl or the like. For example, 1 to 10 parts by weight, specifically, 2 to 9 parts by weight, more specifically, 3 to 8 parts by weight, more specifically, 4 to 7 parts by weight of the active material 13 may be mixed with 1 part by weight of the aerogel. When the aerogel particles 10 simultaneously have hydrophilicity and hydrophobicity, the aerogel particles 10 can be easily mixed with each of a hydrophobic active material or a hydrophilic active material. The active material 13, for example, a hydrophobic active material, specifically, oils, and more specifically, fragrance oils may be supported in the pores 12 of the aerogel particles 10.

Preparation of Aerogel/Hydrogel Composite

Figure 2:
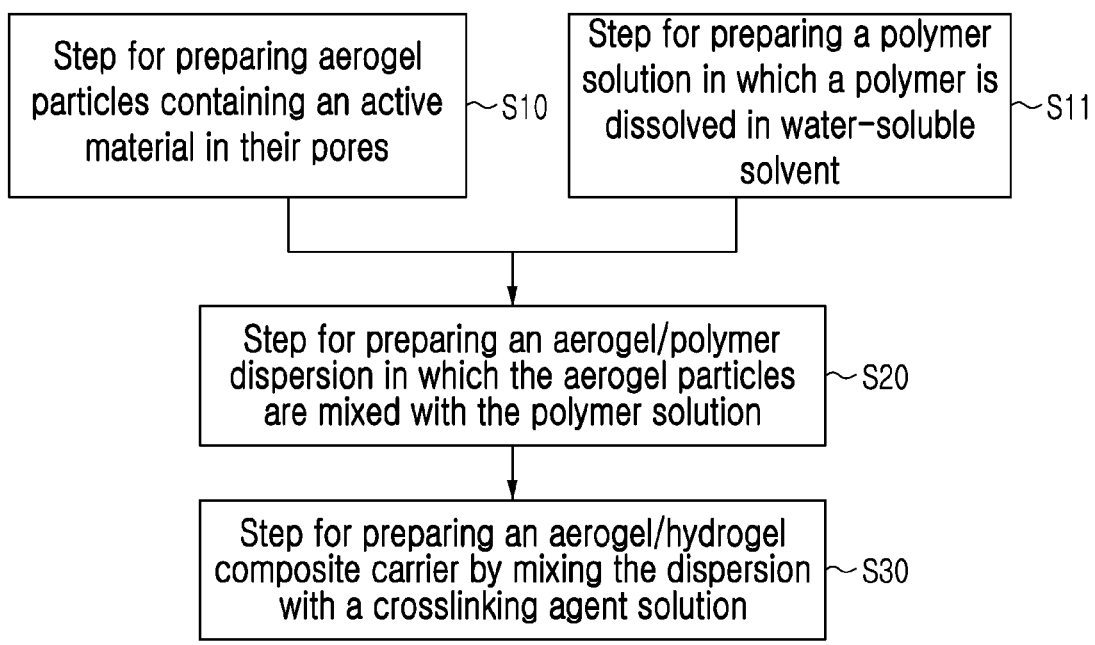
FIG. 2 is a flow chart sequentially showing a method of manufacturing an aerogel/hydrogel composite according to a second embodiment of the present invention.
Figure 3:
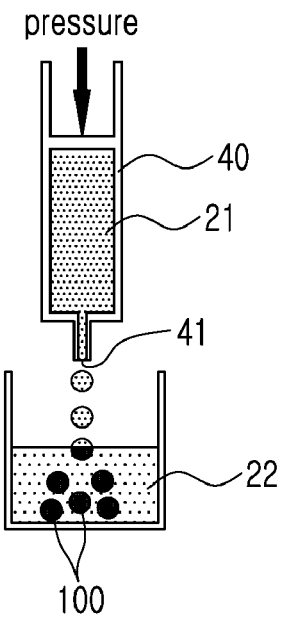
FIG. 3 is a schematic view for step S30 of the method of FIG. 2.

FIG. 2 is a flow chart sequentially showing a method of manufacturing an aerogel/hydrogel composite according to a second embodiment of the present invention, and FIG. 3 is a schematic view for step S30 of the method of FIG. 2.

Referring to FIGS. 2 and 3, the aerogel particles carrying the active material may be prepared (S10) according to the above embodiment described referring to FIG. 1. A polymer can be provided (S11). The polymer may be a hydrophilic polymer, and specifically, the polymer may be prepared as a polymer solution in which the polymer is dissolved in water-soluble solvent, for example, in water.

The polymer can be used as long as it can be dissolved in the water-soluble solvent, and crosslinks can be formed between the chains of the polymer by a crosslinking agent. For example, the polymer may be a natural hydrophilic polymer such as pectin, gelatin, cellulose specifically carboxymethylcellulose (CMC), collagen, dextran, elastin, chitin, chitosan, sodium alginate; or a synthetic hydrophilic polymer such as polyacrylic acid (PAA), polyvinyl alcohol, polyethylene glycol, polyvinyl pyrrolidone, polyurethane, polyhydroxyethyl methacrylate, silicone; or any combinations thereof. For example, the polymer may be sodium alginate.

An aerogel/polymer dispersion 21 in which the aerogel particles specifically, a plurality of the aerogel particles carrying the active material, are mixed in the polymer solution may be prepared (S20). The mixing may be, for example, agitation using a high speed mixer or a ball mill grinder to homogeneously disperse the aerogel particles in the polymer solution. Thus, the plurality of aerogel particles can be evenly mixed without agglomeration in the hydrophilic polymer solution.

For example, the aerogel particles may be mixed in an amount of 0.1 to 10 weight, specifically, 0.1 to 5 weight, and more specifically, 0.1 to 1 weight, based on 10 weight of the polymer aqueous solution. The stirring speed may be 10 rpm to 200 rpm, specifically, 50 rpm to 150 rpm, more specifically, 80 rpm to 100 rpm.

The aerogel/polymer dispersion 21 may be mixed with a crosslinking agent solution 22 to form an aerogel/hydrogel composite carrier 100 (S30). The crosslinking agent solution 22 may be a solution in which a crosslinking agent is dissolved in a solvent, specifically, a water-soluble solvent, for example, water.

The crosslinking agent may be capable of forming a three-dimensional crosslinking (indicated by C in FIG. 3) through chemical bonding to the polymer. The crosslinking agent may be, for example, calcium chloride, calcium sulfate, calcium nitrate, zinc nitrate, zinc chloride, zinc sulfate, ammonium persulfate or glutaraldehyde. The crosslinking agent is not limited thereto, and may vary depending on the type of the polymer. The polymer can be converted into a hydrogel by such crosslinking agents.

For example, the crosslinking of the polymer may be formed by ionic bonding by calcium ions in the crosslinking agent. For example, the crosslinking agent solution 22 may be a calcium chloride aqueous solution. For example, in the crosslinking agent solution 22, the crosslinking agent may be mixed in a weight of 0.01 to 0.1, based on 10 weight of the solvent.

The mixing may be performed by dripping the aerogel/polymer dispersion 21 into the crosslinking agent solution 22. Specifically, the dispersion liquid 21 may be provided in the storage device 40, for example, a pipette, and may be dropped dropwise at a constant size and constant speed into the crosslinking agent solution 22 through the nozzle 41. Accordingly, the aerogel/polymer dispersion 21 may be solidified by reacting with the crosslinking agent solution 22 to form a carrier having a spherical shape, that is, the aerogel/hydrogel composite carrier 100. For example, the average diameter of the aerogel/hydrogel composite carrier 100 may be 100 μm to 10 mm.

Figure 4A:
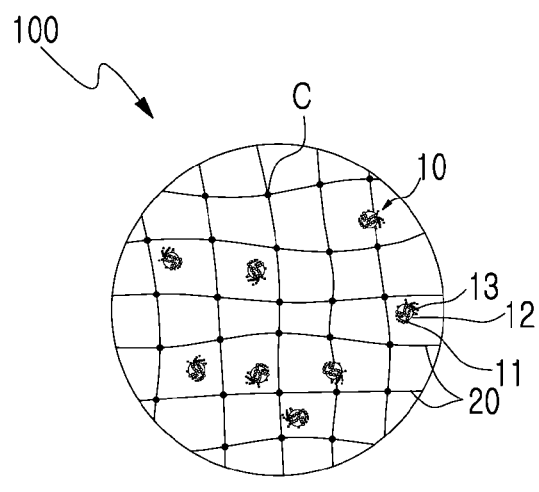
FIG. 4A is a cross-sectional view showing a cross section of the aerogel/hydrogel composite particle according to the first embodiment of the present invention.
Figure 4B:
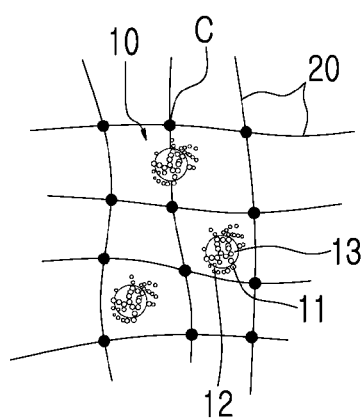
FIG. 4B is an enlarged view of FIG. 4A.

FIG. 4A is a cross-sectional view showing a cross section of the aerogel/hydrogel composite particle according to an embodiment of the present invention, FIG. 4B is an enlarged view of FIG. 4A.

Referring to FIGS. 4A and 4B, the aerogel/hydrogel composite 100 of the present invention includes a hydrogel 20 having a three-dimensional network structure and a plurality of aerogel particles dispersed in the network 10. The aerogel particles 10 may contain an active material 13 in their pores 12.

Specifically, as described above with referring to FIG. 3, when the aerogel/polymer dispersion (21 in FIG. 3) is dripped into the crosslinking agent solution (22 in FIG. 3) drop by drop, the polymer in the aerogel/polymer dispersion (21 in FIG. 3) can be crosslinked by the crosslinking agent. For example, carboxyl groups contained in sodium alginate as an example of the polymer may form ionic bonds with the crosslinking agent, for example, calcium ions of calcium chloride. Accordingly, from the surface to the inner direction of the droplet of dispersion, the polymer may be gradually crosslinked, that is, gelled to form a hydrogel having a three-dimensional network structure, thereby forming a carrier having an approximately spherical shape. At this time, a plurality of aerogel particles 10 evenly dispersed in the dispersion 21 may be evenly distributed in the hydrogel 20 network structure.

In other words, the aerogel/hydrogel composite 100 of the present invention, that is, the aerogel/hydrogel composite carrier 100 may have a plurality of aerogel particles 10 positioned within the network structure of the hydrophilic hydrogel 20, the aerogel particles 10 cannot be aggregated with each other, and may be evenly dispersed in the hydrogel 20. Specifically, the plurality of aerogel particles can be homogeneously dispersed in the polymer solution through the high-speed stirring described above, and the plurality of aerogel particles can maintain a homogeneously dispersed state without agglomeration to each other in the network structure of hydrogel 20 which is formed through crosslinking by the crosslinking agent, specifically, crosslinking (C) by calcium ions in the crosslinking agent.

Therefore, the aerogel/hydrogel composite carrier 100 may absorb or contain a large amount of moisture by the hydrogel 20, and may include the active material 13, specifically a hydrophobic active material that exhibits functionality, absorbed and contained in the pores 12 in the aerogel particles 10. Accordingly, the active material 13 may be homogeneously dispersed in the network structure of the hydrogel 20.

In addition, the stability of the network structure of the hydrogel 20 in the composite carrier 100 may compensate for the low mechanical properties of the aerogel particles 10, and water and oil can be stably contained at the same time in the aerogel/hydrogel composite carrier. Therefore, it is possible to provide a composite carrier 100 having improved properties such as low density, high strength, high component content, and stable desorption.

The composite carrier 100 may be applied to various fields such as food, cosmetics, biochemistry, and pharmaceuticals, and may be used as, for example, a diffuser, fragrance, perfume, cosmetics, and nutritional supplements.

Hereinafter, preferred examples are provided to aid the understanding of the present invention. However, the following experimental example is only for helping understanding of the present invention, and the present invention is not limited by the following experimental example.

Preparation Examples of Aerogel Carrying Active Material

Preparation Example 1: Preparation of an Aerogel (Hybrid Aerogel Particles) Carrying an Active Material A hydrophobic aerogel having a trimethylsilyloxy group ($-OSi(CH_3)_3$) on the surface was placed in an electric furnace in an oxidizing atmosphere, heated to 345° C., and then sintered for 1 hour while maintaining this temperature, thereby producing a hybrid aerogel. 0.5 g of the prepared hybrid aerogel and 4.375 g of essential oil (peach flavor oil) were mixed in a bowl.

Preparation Example 2: Preparation of an Aerogel (Hydrophobic Aerogel Particles) Carrying an Active Material An aerogel carrying an active material was prepared in the same manner as in Preparation Example 1, except that 1.0 g of a hydrophobic aerogel instead of the hybrid aerogel and 3.5 g of the essential oil were mixed.

Preparation Example of Aerogel/Hydrogel Complex

A transparent sodium alginate aqueous solution was prepared by mixing 5 g of sodium alginate and 95 g of water at 80° C. for 3 hours using an electronic stirrer. Aerogel particles were prepared by mixing 1 g of crushed silica aerogel powder in a bowl with 3 g of lavender oil. The sodium alginate aqueous solution and the aerogel particles were mixed using a ball mill grinder for 3 hours to prepare an aerogel/sodium alginate dispersion. Meanwhile, a transparent calcium chloride aqueous solution was prepared by mixing 5 g of calcium chloride and 200 g of water using an electronic stirrer. Thereafter, the aerogel/sodium alginate dispersion was dropped into the calcium chloride aqueous solution through a pipette. When the aerogel/sodium alginate dispersion was dropped into the calcium chloride solution, it solidified to produce an aerogel/hydrogel composite carrier having a perfume function.

Aerogel Surface Modification Example 1

A hydrophobic aerogel powder having a trimethylsilyloxy group ($-OSi(CH_3)_3$) on the surface was placed in an electric furnace in an oxidizing atmosphere and heated to 340° C., followed by sintering for 1 hour while maintaining this temperature.

Aerogel Surface Modification Example 2

The hydrophobic aerogel powder was sintered in the same manner as in Aerogel surface modification example 1, except that it was sintered at 350° C.

Aerogel Surface Modification Example 3

The hydrophobic aerogel powder was sintered in the same manner as in Aerogel surface modification example 1, except that it was sintered at 360° C.

Figure 5A:
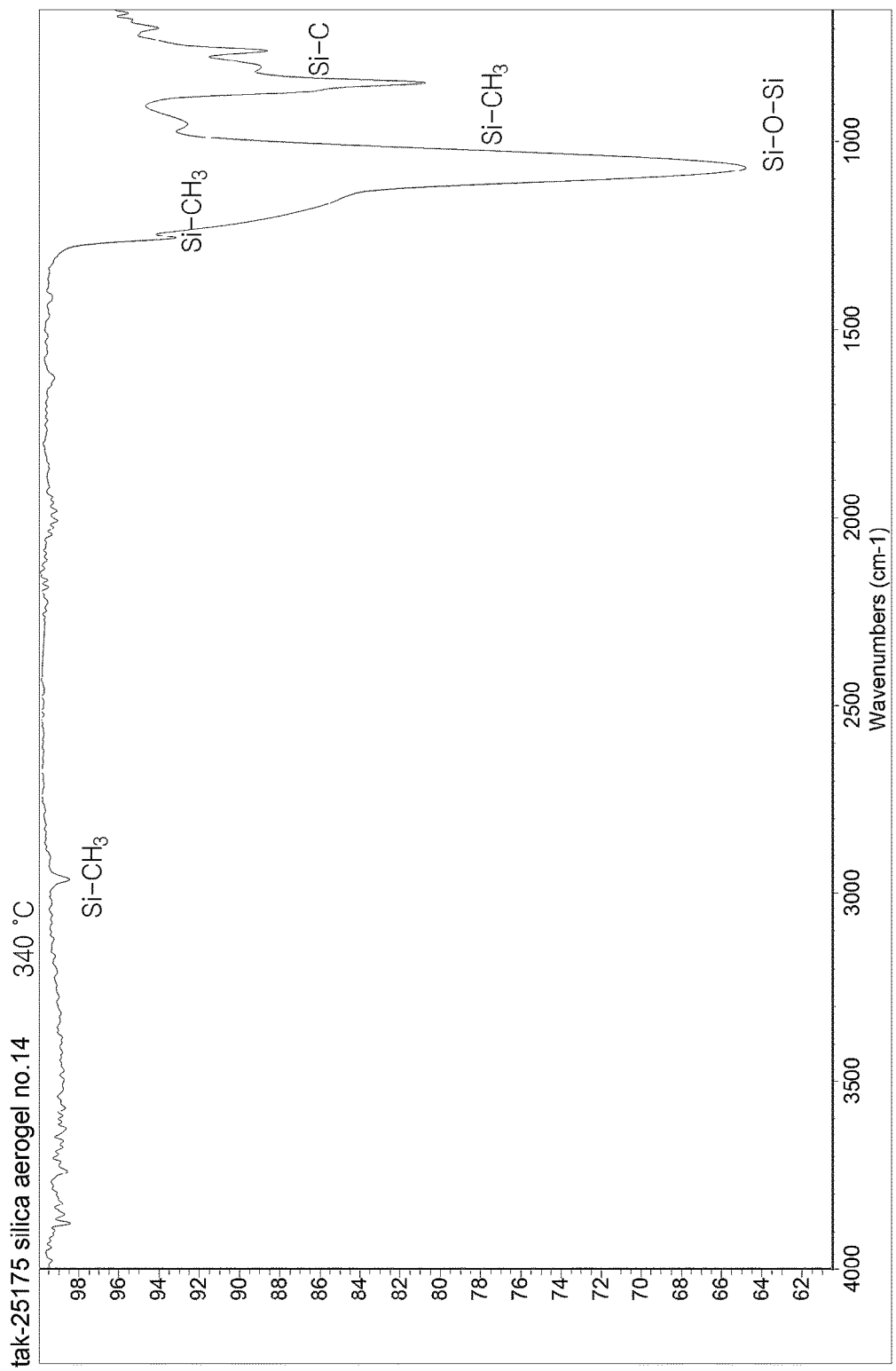
FIGS. 5A to 5C are graphs illustrating measurement results of the powders obtained in Aerogel surface modification example 1 to 3, respectively, through Fourier-transform infrared spectroscopy (FT-IR spectroscopy).
Figure 5B:
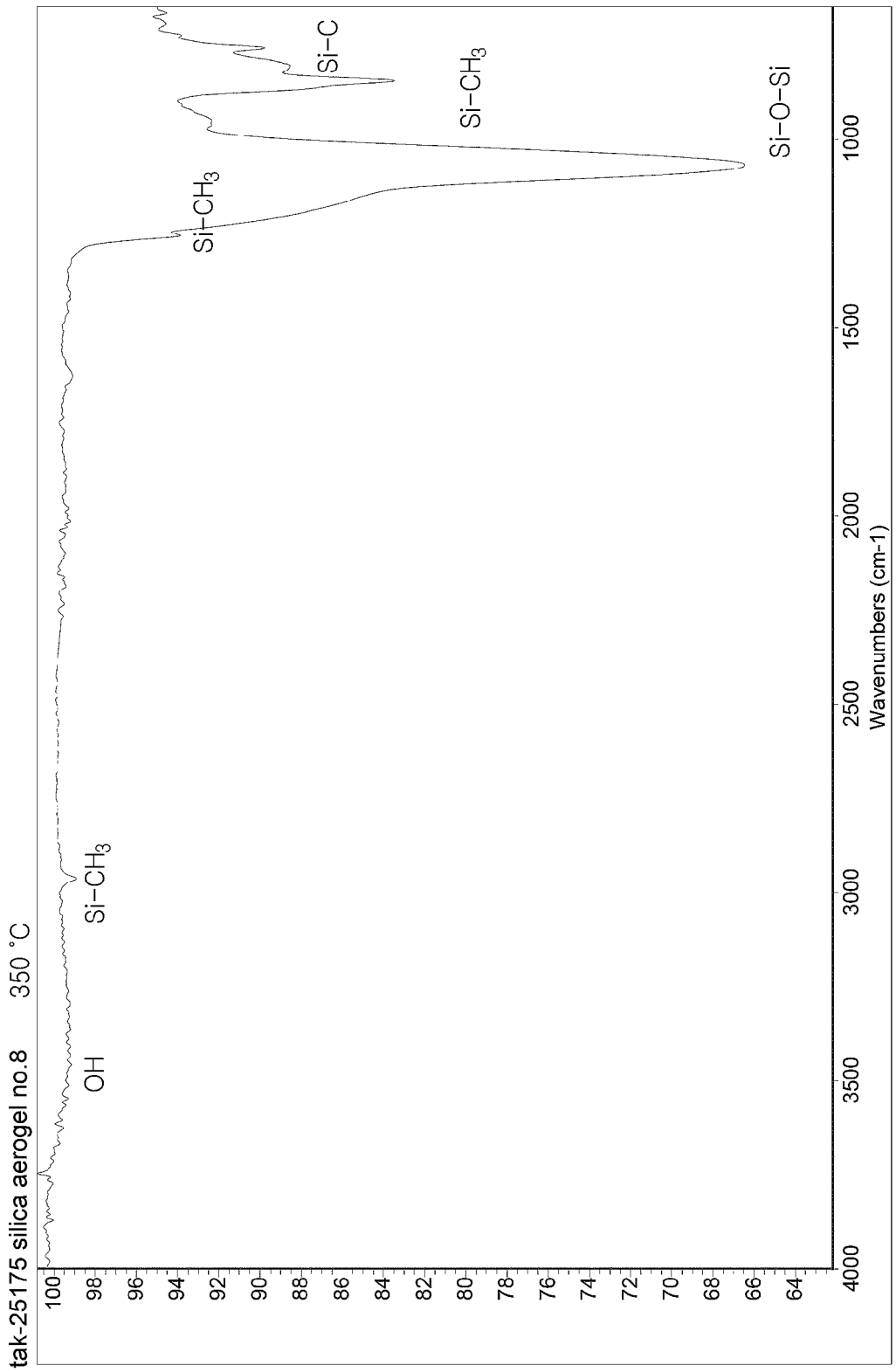
Figure 5C:
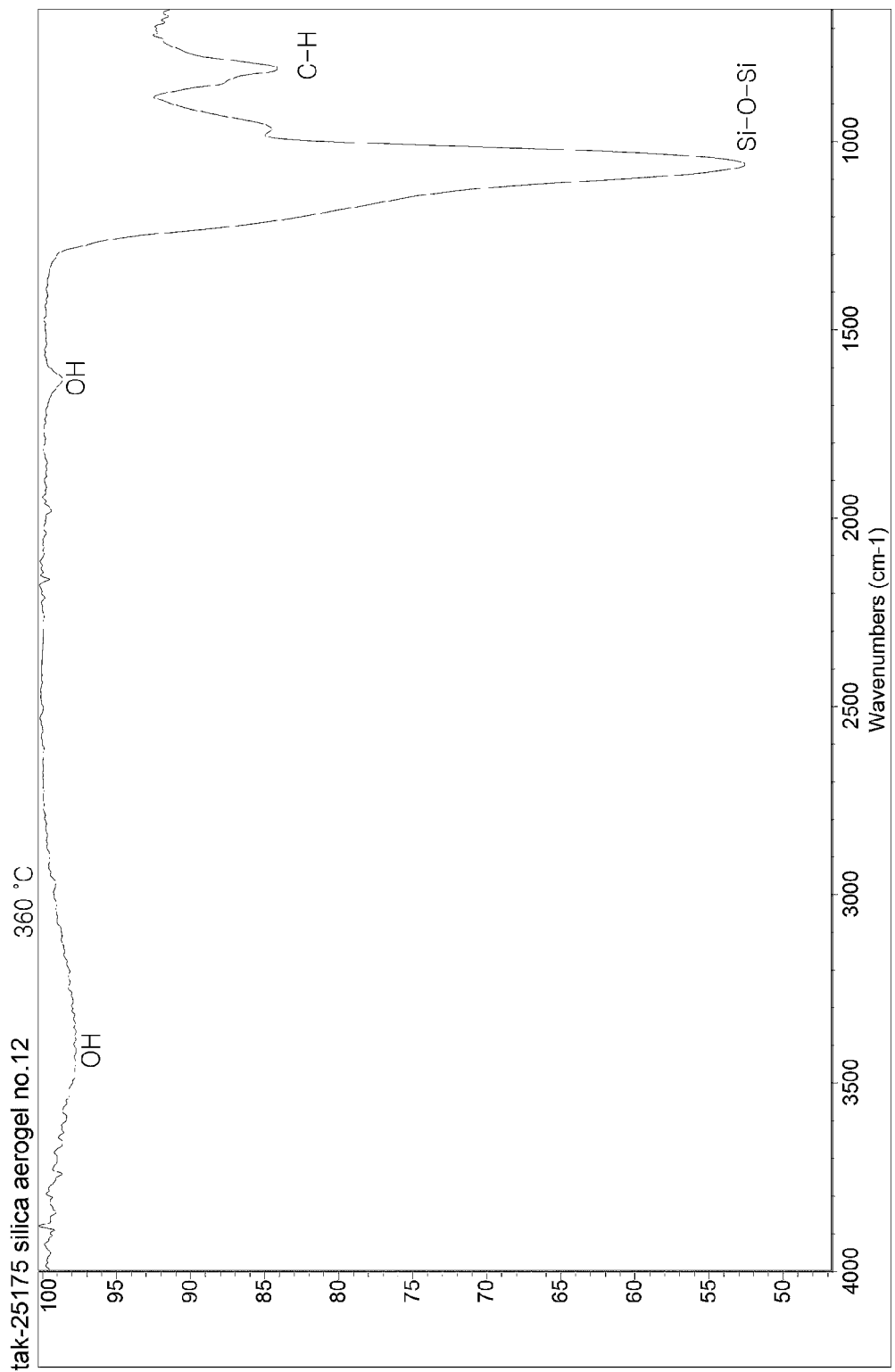

FIGS. 5A to 5C are graphs illustrating measurement results of the powders obtained in Aerogel surface modification example 1 to 3, respectively, using Fourier-transform infrared spectroscopy (FT-IR spectroscopy).

Referring to FIG. 5A, it can be seen that the aerogel according to Aerogel surface modification example 1 shows a Si—$CH_3$ group in addition to a Si—O—Si group inherent in silica, indicating that the aerogel remains as a hydrophobic aerogel having a hydrophobic surface despite heat treatment.

Referring to FIG. 5B, it can be seen that the aerogel according to Aerogel surface modification example 2 shows both a Si—$CH_3$ group and an OH group in addition to a Si—O—Si group inherent in silica, indicating that the aerogel is hybrid aerogel formed by partially modifying the hydrophobic surface into a hydrophilic surface through thermal treatment.

Referring to FIG. 5C, it can be seen that the aerogel according to Aerogel surface modification example 3 shows an OH group in addition to a Si—O—Si group inherent in silica, and that a peak corresponding to a Si—$CH_3$ group, which has been observed before surface modification, completely disappears, indicating that the aerogel is converted into hydrophilic aerogel formed by completely modifying the hydrophobic surface into a hydrophilic surface through thermal treatment.

Figure 6:
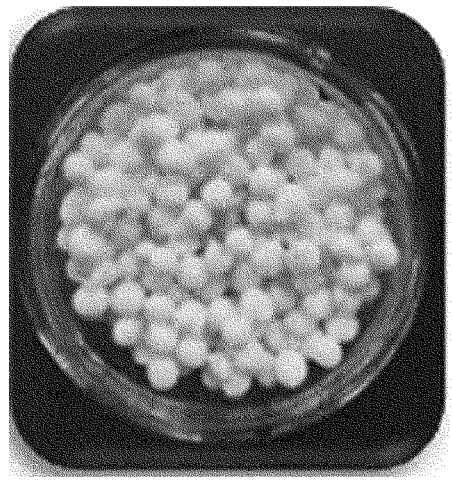
FIG. 6 is a photograph of the aerogel/hydrogel composite carrier according to the Preparation Example 2.

FIG. 6 is a photograph of the aerogel/hydrogel composite carrier prepared according to the Preparation example of aerogel/hydrogel complex of the present invention.

Referring to FIG. 6, it was confirmed that an aerogel/hydrogel composite carrier having a spherical shape was prepared.

EXPERIMENTAL EXAMPLES: ANALYSIS OF SCENTING PROPERTIES

Experimental Example 1: Analysis of Scenting Properties (1)—Preparation Example 1 and Comparative Example The aerogel of Preparation Example 1 was placed at room temperature (25° C.) while scenting (evaporation) properties specifically, evaporation amount per day (g), cumulative evaporation amount (g), and evaporation rate (%) were measured according to the elapsed time (21 days). For an accurate comparison, the scenting properties of pure essential oil (4.375 g) (Comparative Example) without aerogel complex were compared. In addition, in order to reduce the error, Sample 1 and Sample 2 were prepared according to Preparation Example 1, and then their average values were calculated. Samples 1 and 2 (Oil containing Hybrid A/G) were prepared by mixing 0.5 g of hybrid aerogel and 4.375 g of essential oil, as described above.

Figure 7:
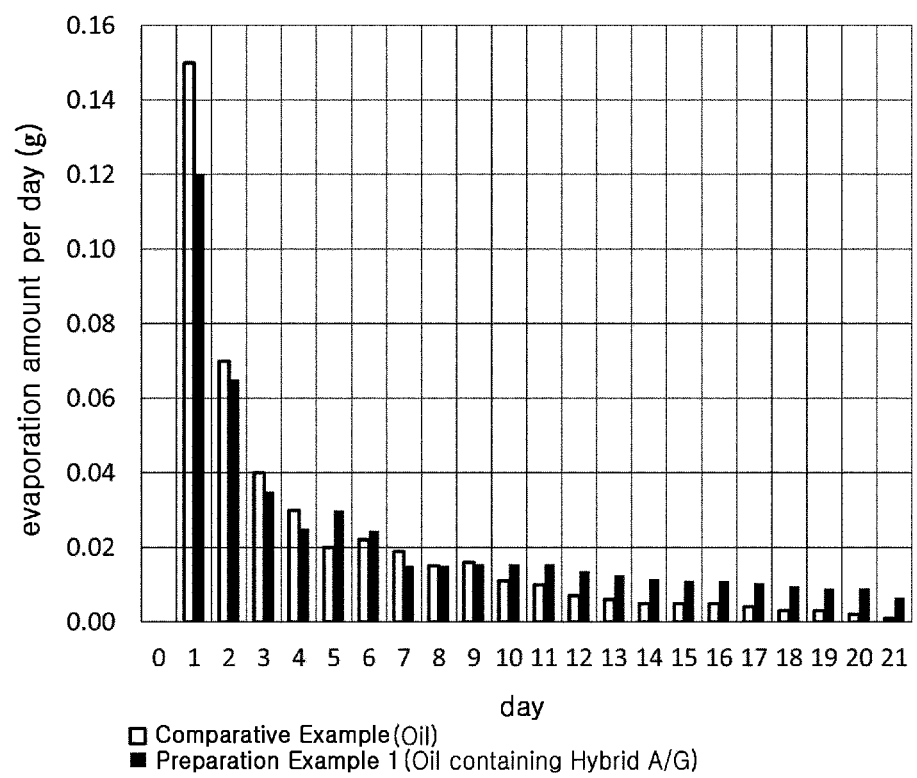
FIG. 7 is a graph showing the amount of evaporation per day (g) among the results of Experimental Example 1.
Figure 8:
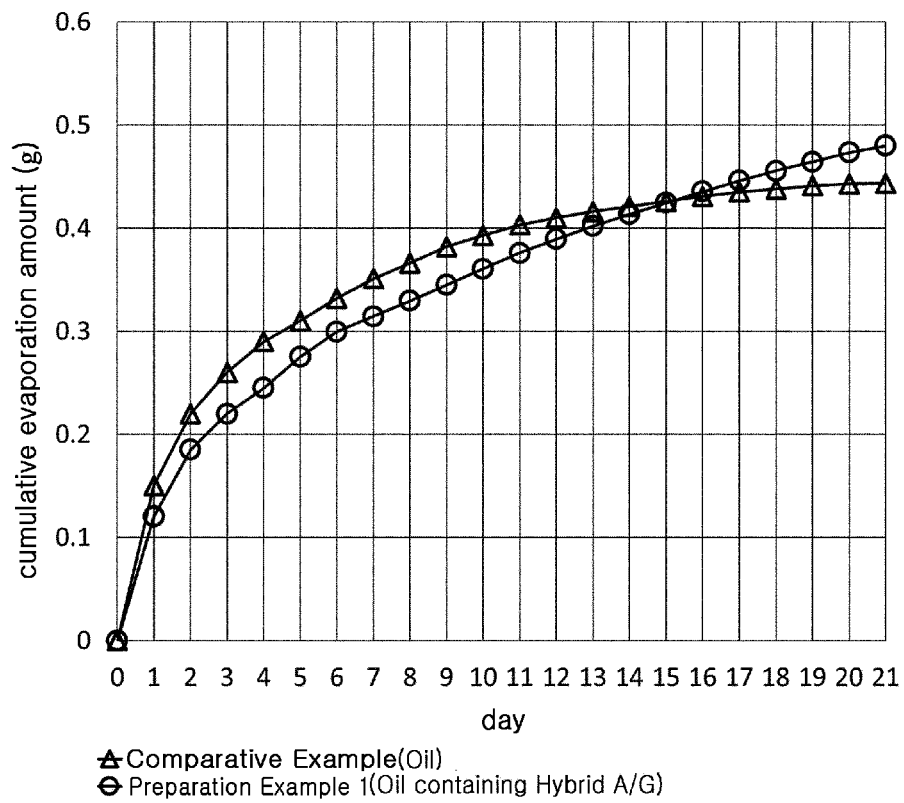
FIG. 8 is a graph showing the amount of cumulative evaporation (g) among the results of Experimental Example 1.
Figure 9:
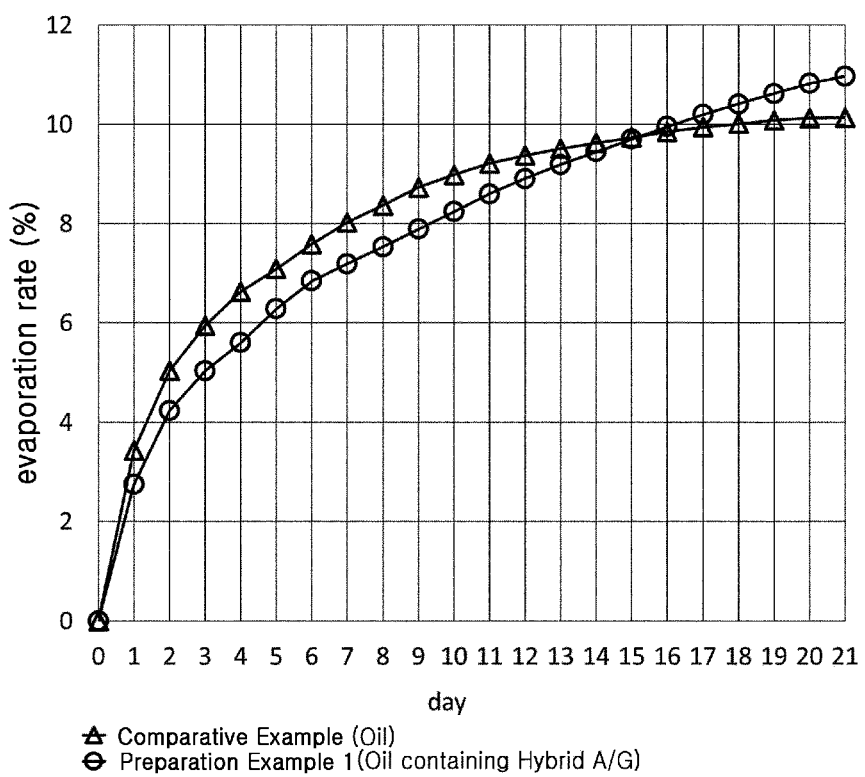
FIG. 9 is a graph showing the rate of evaporation (%) among the results of Experimental Example 1.

Tables 1 to 3 show the results of Experimental Example 1, evaporation amount per day (g), cumulative evaporation amount (g) and evaporation rate (%), respectively. FIGS. 7 to 9 are graphs showing the amount of evaporation per day (g), the amount of cumulative evaporation (g), and the rate of evaporation (%), respectively. (amount of evaporation per day (g) (FIG. 7), amount of cumulative evaporation (g) (FIG. 8), the rate of evaporation (%) (FIG. 9))

TABLE 1 the amount of evaporation per day (g) - Preparation Example 1 and Comparative Example

| elapsed time (day) | Comparative Example (oil) | Average value of Samples 1 and 2 | Preparation Example 1 (Oil containing Hybrid A/G) Sample 1 | Preparation Example 1 (Oil containing Hybrid A/G) Sample 2 |
|---|---|---|---|---|
| 0 | 0.0000 g | 0.0000 g | 0.0000 g | 0.0000 g |
| 1 | 0.1500 g | 0.1200 g | 0.1300 g | 0.1100 g |
| 2 | 0.0700 g | 0.0650 g | 0.0700 g | 0.0600 g |
| 3 | 0.0400 g | 0.0350 g | 0.0300 g | 0.0400 g |
| 4 | 0.0300 g | 0.0250 g | 0.0300 g | 0.0200 g |
| 5 | 0.0200 g | 0.0300 g | 0.0200 g | 0.0400 g |
| 6 | 0.0220 g | 0.0245 g | 0.0230 g | 0.0260 g |
| 7 | 0.0190 g | 0.0150 g | 0.0150 g | 0.0150 g |
| 8 | 0.0150 g | 0.0150 g | 0.0150 g | 0.0150 g |
| 9 | 0.0160 g | 0.0155 g | 0.0150 g | 0.0160 g |
| 10 | 0.0110 g | 0.0155 g | 0.0150 g | 0.0160 g |
| 11 | 0.0100 g | 0.0155 g | 0.0150 g | 0.0160 g |
| 12 | 0.0070 g | 0.0135 g | 0.0140 g | 0.0130 g |
| 13 | 0.0060 g | 0.0125 g | 0.0130 g | 0.0120 g |
| 14 | 0.0050 g | 0.0115 g | 0.0120 g | 0.0110 g |
| 15 | 0.0050 g | 0.0110 g | 0.0110 g | 0.0110 g |
| 16 | 0.0050 g | 0.0110 g | 0.0110 g | 0.0110 g |
| 17 | 0.0040 g | 0.0105 g | 0.0110 g | 0.0100 g |
| 18 | 0.0030 g | 0.0095 g | 0.0100 g | 0.0090 g |
| 19 | 0.0030 g | 0.0090 g | 0.0090 g | 0.0090 g |
| 20 | 0.0020 g | 0.0090 g | 0.0090 g | 0.0090 g |
| 21 | 0.0010 g | 0.0065 g | 0.0070 g | 0.0060 g |

Referring to Table 1 and FIG. 7 together, it can be confirmed that, in the case of pure oil, which is Comparative Example, the initial evaporation amount per day (Day 1 to Day 4) is greater than that of Preparation Example 1, but the evaporation amount per day is markedly reduced after 10 days, and there is very little evaporation after 21 days elapsed. On the other hand, in the case of the hybrid aerogel of Preparation Example 1, it can be confirmed that even after 20 days, the amount of evaporation per day remains almost unchanged, and it is possible to continue to scent even after 21 days.

TABLE 2 the amount of cumulative evaporation (g) - Preparation Example 1 and Comparative Example

| elapsed time (day) | Comparative Example (oil) | Average value of Samples 1 and 2 | Preparation Example 1 (Oil containing Hybrid A/G) Sample 1 | Preparation Example 1 (Oil containing Hybrid A/G) Sample 2 |
|---|---|---|---|---|
| 0 | 0.0000 g | 0.0000 g | 0.0000 g | 0.0000 g |
| 1 | 0.1500 g | 0.1200 g | 0.1300 g | 0.1100 g |
| 2 | 0.2200 g | 0.1850 g | 0.2000 g | 0.1700 g |
| 3 | 0.2600 g | 0.2200 g | 0.2300 g | 0.2100 g |
| 4 | 0.2900 g | 0.2450 g | 0.2600 g | 0.2300 g |
| 5 | 0.3100 g | 0.2750 g | 0.2800 g | 0.2700 g |
| 6 | 0.3320 g | 0.2995 g | 0.3030 g | 0.2960 g |
| 7 | 0.3510 g | 0.3145 g | 0.3180 g | 0.3110 g |
| 8 | 0.3660 g | 0.3295 g | 0.3330 g | 0.3260 g |
| 9 | 0.3820 g | 0.3450 g | 0.3480 g | 0.3420 g |
| 10 | 0.3930 g | 0.3605 g | 0.3630 g | 0.3580 g |
| 11 | 0.4030 g | 0.3760 g | 0.3780 g | 0.3740 g |
| 12 | 0.4100 g | 0.3895 g | 0.3920 g | 0.3870 g |
| 13 | 0.4160 g | 0.4020 g | 0.4050 g | 0.3990 g |
| 14 | 0.4210 g | 0.4135 g | 0.4170 g | 0.4100 g |
| 15 | 0.4260 g | 0.4245 g | 0.4280 g | 0.4210 g |
| 16 | 0.4310 g | 0.4355 g | 0.4390 g | 0.4320 g |
| 17 | 0.4350 g | 0.4460 g | 0.4500 g | 0.4420 g |
| 18 | 0.4380 g | 0.4555 g | 0.4600 g | 0.4510 g |
| 19 | 0.4410 g | 0.4645 g | 0.4690 g | 0.4600 g |
| 20 | 0.4430 g | 0.4735 g | 0.4780 g | 0.4690 g |
| 21 | 0.4435 g | 0.4800 g | 0.4850 g | 0.4750 g |

Referring to Table 2 and FIG. 8 together, as shown in FIG. 7, in the case of pure oil, which is Comparative Example, as the amount of evaporation per day significantly decreases after 10 days, the cumulative amount of evaporation becomes saturated after 17 days, whereas in the case of hybrid aerogel of Preparation Example 1, it can be confirmed that the cumulative evaporation amount is steadily increasing even after 21 days have elapsed. As a result, it can be seen that the hybrid aerogel of the present invention has an excellent effect of sustaining fragrance compared to the essential oil itself

TABLE 3 the rate of evaporation (%) - Preparation Example 1 and Comparative Example

| elapsed time (day) | Comparative Example (oil) | Average value of Samples 1 and 2 | Preparation Example 1 (Oil containing Hybrid A/G) Sample 1 | Preparation Example 1 (Oil containing Hybrid A/G) Sample 2 |
|---|---|---|---|---|
| 0 | 0.0000% | 0.0000% | 0.0000% | 0.0000% |
| 1 | 3.4286% | 2.7429% | 2.9714% | 2.5143% |
| 2 | 5.0286% | 4.2286% | 4.5714% | 3.8857% |
| 3 | 5.9429% | 5.0286% | 5.2571% | 4.8000% |
| 4 | 6.6286% | 5.6000% | 5.9429% | 5.2571% |
| 5 | 7.0857% | 6.2857% | 6.4000% | 6.1714% |
| 6 | 7.5886% | 6.8457% | 6.9257% | 6.7657% |
| 7 | 8.0229% | 7.1886% | 7.2686% | 7.1086% |
| 8 | 8.3657% | 7.5314% | 7.6114% | 7.4514% |
| 9 | 8.7314% | 7.8857% | 7.9543% | 7.8171% |
| 10 | 8.9829% | 8.2400% | 8.2971% | 8.1829% |
| 11 | 9.2114% | 8.5943% | 8.6400% | 8.5486% |
| 12 | 9.3714% | 8.9029% | 8.9600% | 8.8457% |
| 13 | 9.5086% | 9.1886% | 9.2571% | 9.1200% |
| 14 | 9.6229% | 9.4514% | 9.5314% | 9.3714% |
| 15 | 9.7371% | 9.7029% | 9.7829% | 9.6229% |
| 16 | 9.8514% | 9.9543% | 10.0343% | 9.8743% |
| 17 | 9.9429% | 10.1943% | 10.2857% | 10.1029% |
| 18 | 10.0114% | 10.4114% | 10.5143% | 10.3086% |
| 19 | 10.0800% | 10.6171% | 10.7200% | 10.5143% |
| 20 | 10.1257% | 10.8229% | 10.9257% | 10.7200% |
| 21 | 10.1371% | 10.9714% | 11.0857% | 10.8571% |

Referring to Table 3 and FIG. 9 together, in the case of the pure oil of Comparative Example, the evaporation rate did not increase any more after 17 days, whereas in the case of the hybrid aerogel of Preparation Example 1, the evaporation rate steadily increased even after 21 days. As a result, it can be seen that the hybrid aerogel of the present invention has excellent scenting performance as well as excellent constant scenting compared to the existing essential oil.

Experimental Example 2: Analysis of Scenting Properties (2)—Preparation Example 1 and Preparation Example 2

The scenting properties of aerogel composites according to Preparation Example 1 and Preparation Example 2 were analyzed in the same manner as in Experimental Example 1 except as described below.

Hybrid aerogel composite of Preparation Example 1 was prepared using 1.0 g of the hybrid aerogel and 3.5 g of essential oil, which are different in content from the abovementioned Preparation Example 1. As Comparative Example, pure essential oil 3.5 g was used. The elapsed time of fragrance was 7 days.

Figure 10:
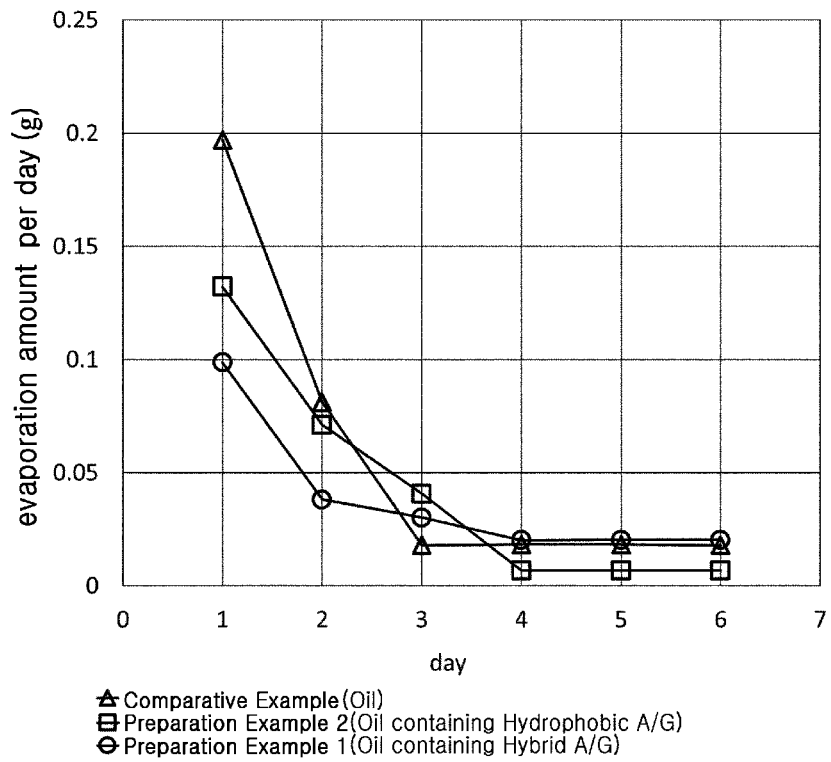
FIG. 10 is a graph showing the amount of evaporation per day (g) among the results of Experimental Example 2.
Figure 11:
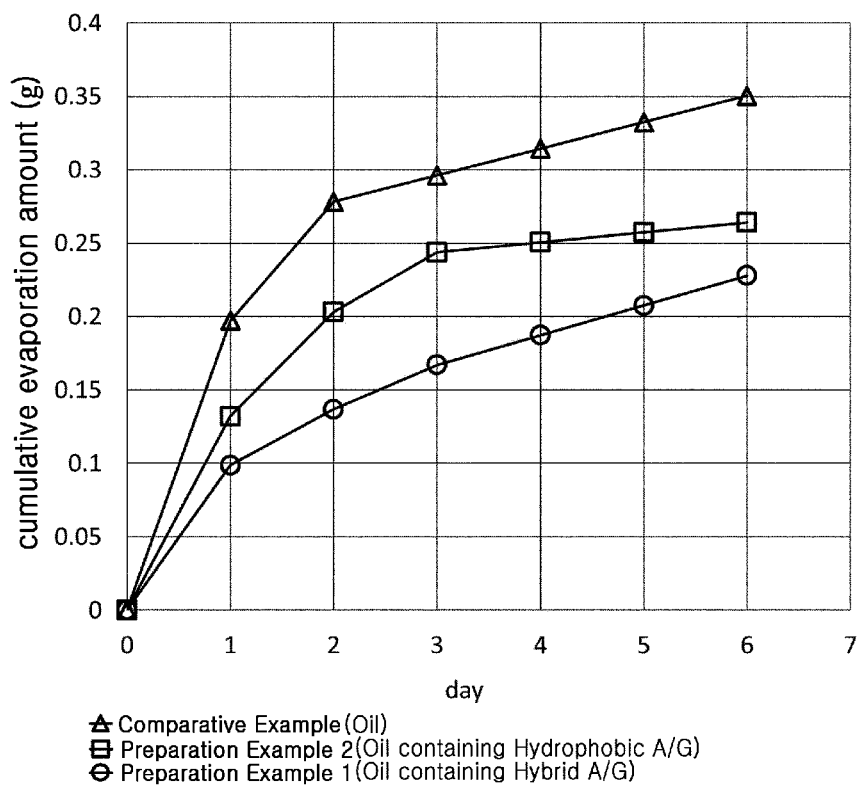
FIG. 11 is a graph showing the amount of cumulative evaporation (g) among the results of Experimental Example 2.
Figure 12:
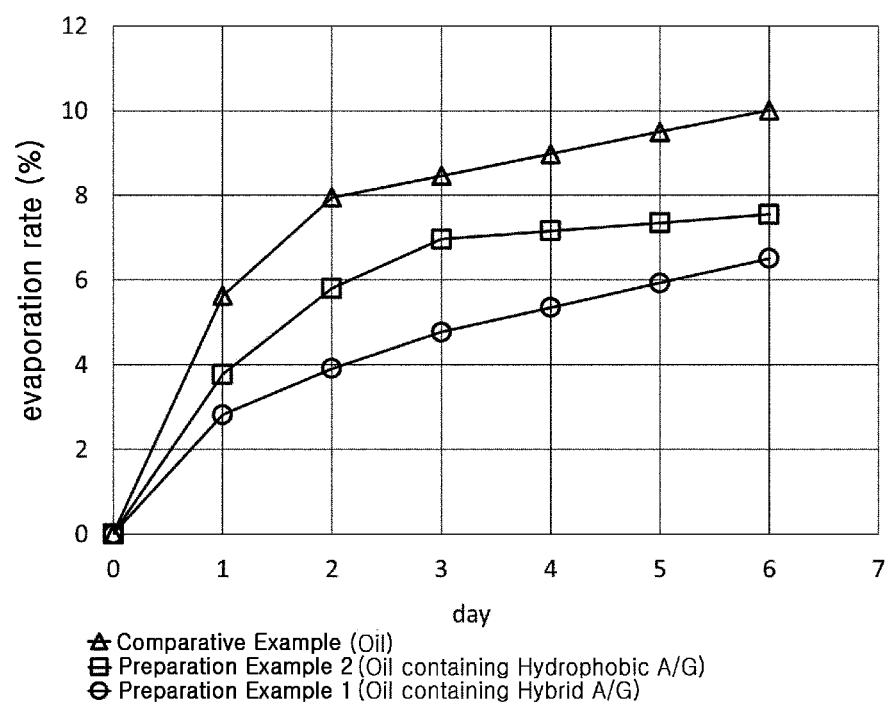
FIG. 12 is a graph showing the rate of evaporation (%) among the results of Experimental Example 2.

Tables 4 to 6 respectively show the results of Experimental Example 2, evaporation amount per day (g), cumulative evaporation amount (g) and evaporation rate (%), respectively. FIGS. 10 to 12 are graphs showing the amount of evaporation per day (g), the amount of cumulative evaporation (g), and the rate of evaporation (%), respectively. (amount of evaporation per day (g) (FIG. 10), amount of cumulative evaporation (g) (FIG. 11), rate of evaporation (%) (FIG. 12))

TABLE 4 the amount of evaporation per day (g) - Preparation Example 1, Preparation Example 2, and Comparative Example

| elapsed time (day) | Comparative Example (oil) | Preparation Example 1 (Oil containing Hybrid A/G) | Preparation Example 2 (Oil containing Hydrophobic A/G) |
|---|---|---|---|
| 0 | 0.0000 g | 0.0000 g | 0.0000 g |
| 1 | 0.1971 g | 0.0987 g | 0.1321 g |
| 2 | 0.0812 g | 0.0382 g | 0.0711 g |
| 3 | 0.0178 g | 0.0302 g | 0.0406 g |
| 4 | 0.0182 g | 0.0202 g | 0.0068 g |
| 5 | 0.0182 g | 0.0203 g | 0.0068 g |
| 6 | 0.0179 g | 0.0203 g | 0.0068 g |

Referring to Table 4 and FIG. 10 together, in the cases of pure oil of Comparative Example and hydrophobic aerogel composite of Preparation Example 2, it can be confirmed that the initial evaporation amount (for about 2 days) is higher than that of hybrid aerogel composite of Preparation Example 1. In particular, the Comparative Example shows highest initial evaporation amount, it is assumed that the evaporation of the pure oil occurs without being disturbed by the aerogel particles.

However, it can be seen that the evaporation amount of Comparative Example and Preparation Example 2 is reduced with a very large change compared to Preparation Example 1 from the 3rd and 4th days. In particular, in the case of the hydrophobic aerogel of Preparation Example 2, the amount of evaporation per day was the lowest after the fourth day, and thus, it is confirmed that the persistence of the fragrance of the hydrophobic aerogel is the inferior.

On the other hand, in the case of the hybrid aerogel composite of Preparation Example 1, the initial evaporation amount was less than those of Comparative Example and Preparation Example 2, but it is found that the evaporation amount is not significantly reduced and maintained at the highest evaporation amount after the 4th day even if time is elapsed.

TABLE 5 the amount of cumulative evaporation (g) - Preparation Example 1, Preparation Example 2, and Comparative Example

| elapsed time (day) | Comparative Example (oil) | Preparation Example 1 (Oil containing Hybrid A/G) | Preparation Example 2 (Oil containing Hydrophobic A/G) |
|---|---|---|---|
| 0 | 0.0000 g | 0.0000 g | 0.0000 g |
| 1 | 0.1971 g | 0.0987 g | 0.1321 g |
| 2 | 0.2783 g | 0.1369 g | 0.2032 g |
| 3 | 0.2961 g | 0.1670 g | 0.2438 g |
| 4 | 0.3143 g | 0.1873 g | 0.2506 g |
| 5 | 0.3325 g | 0.2076 g | 0.2574 g |
| 6 | 0.3504 g | 0.2279 g | 0.2641 g |

Referring to Table 5 and FIG. 11 together, in the case of the hydrophobic aerogel of Preparation Example 2, as shown in FIG. 10, as the amount of evaporation per day markedly decreased after Day 4, the cumulative evaporation amount increased little after Day 4. When comparing pure oil of Comparative Example and the hybrid aerogel of Preparation Example 1, as the time elapsed, it can be confirmed that in the case of Production Example 1, the increase rate of the cumulative evaporation amount was larger. That is, Preparation Example 1 shows that the amount of evaporation per day is kept more constant than Comparative Example. Thus, the hybrid aerogel according to the present invention shows that the amount of evaporation can be controlled by adjusting the amount and fraction of oil and aerogel powder.

TABLE 6 the rate of evaporation (%) - Preparation Example 1, Preparation Example 2, and Comparative Example

| Elapsed Time (day) | Comparative Example (oil) | Preparation Example 1 (Oil containing Hybrid A/G) | Preparation Example 2 (Oil containing Hydrophobic A/G) |
|---|---|---|---|
| 0 | 0.0000% | 0.0000% | 0.0000% |
| 1 | 5.6300% | 2.8200% | 3.7734% |
| 2 | 7.9500% | 3.9100% | 5.8052% |
| 3 | 8.4600% | 4.7723% | 6.9662% |
| 4 | 8.9800% | 5.3507% | 7.1597% |
| 5 | 9.5000% | 5.9300% | 7.3532% |
| 6 | 10.0100% | 6.5100% | 7.5467% |

Referring to Table 6 and FIG. 12, in case of Preparation Example 2 using hydrophobic aerogel, it can be seen that the scenting performance is not good because the evaporation rate does not increase any more as the rapid decrease in the amount of evaporation per day.

In the case of Comparative Example, it is interpreted that the supported oil is quickly consumed due to the higher evaporation rate than in Preparation Example 1, although the variation in evaporation rate is almost constant over the course of 6 days.

On the other hand, in the case of Preparation Example 1, it can be confirmed that the change of the evaporation rate remains constant over the elapsed time of 6 days, and accordingly, it is confirmed that the amount of cumulative evaporation and the evaporation rate are steadily rising. That is, compared to Comparative Example, Preparation Example 1 of the present invention shows that it is possible to sustain scent for a long time and to exhibit excellent scent performance consistently for a long time.

Thus, in the case of Preparation Example 1, it can be seen that the evaporation amount and the evaporation rate can be controlled according to the respective amounts and fractions of the hybrid aerogel and oil, and thus the scent performance and the scent duration can be optimized.

In the above, the present invention has been described in detail with reference to preferred embodiments, but the present invention is not limited to the above embodiments, and various modifications and changes by those skilled in the art is possible within the spirit and scope of the present invention.

The invention claimed is:

1. A method of preparing an aerogel/hydrogel composite comprising:
preparing a plurality of aerogel particles including an aerogel particle having particle clusters and pores formed in a porous network of the particle clusters, and an active material supported in the pores for supplying fragrance;
preparing a polymer solution in which a polymer is dissolved in a water-soluble solvent;
mixing the plurality of aerogel particles into the polymer solution, and then homogenizing the mixture to prepare an aerogel/polymer dispersion; and mixing the dispersion with a crosslinking agent solution to prepare an aerogel/hydrogel composite carrier, wherein the aerogel particles are hybrid aerogel particles having a Si—$CH_3$ group and an OH group in addition to a Si—O—Si group.

2. The method according to claim 1, wherein 1 to 10 parts by weight of the active material is mixed with 1 part by weight of the aerogel particles in the step of preparing the plurality of aerogel particles.

3. The method according to claim 1, wherein the active material is a natural extract, a natural extract oil, an alcohol having 1 to 40 carbon atoms, an alkane or an organic compound having an ester functional group having 4 to 40 carbon atoms.

4. The method according to claim 1, wherein the polymer is dissolved in the water-soluble solvent and forms a crosslink by the crosslinking agent in the crosslinking agent solution.

5. The method according to claim 1, wherein 0.1 to 10 parts by weight of the aerogel particles is mixed with 10 part by weight of polymer solution.

6. The method according to claim 1, wherein the aerogel/polymer dispersion is dripped into the crosslinking agent solution to form the carrier having a spherical shape when the aerogel/hydrogel composite carrier is prepared.

7. The method according to claim 6, wherein the aerogel/hydrogel composite carrier includes the hydrogel having a three-dimensional network structure formed by crosslinking the polymer and the plurality of aerogel particles dispersed in the network structure.

8. An aerogel/hydrogel composite comprising:
a hydrogel having a three-dimensional network structure; and
a plurality of aerogel particles including an aerogel particle having particle clusters and pores formed in a porous network of the particle clusters, and an active material supported in the pores for supplying fragrance,
wherein the aerogel particle are hybrid aerogel particles having a Si—$CH_3$ group and an OH group in addition to a Si—O—Si group.

9. The aerogel/hydrogel composite according to claim 8, wherein the active material is a natural extract, a natural extract oil, an alcohol having 1 to 40 carbon atoms, an alkane or an organic compound having an ester functional group having 4 to 40 carbon atoms.

10. The aerogel/hydrogel composite according to claim 9, wherein the composite is a carrier having a spherical shape.

11. Aerogel comprising:
an aerogel particle having particle clusters and pores formed in a porous network of the particle clusters; and
an active material supported in the pores for supplying fragrance,
wherein the aerogel particle is a hybrid aerogel particle having a Si—$CH_3$ group and an OH group in addition to a Si—O—Si group.

\* \* \* \* \*